United States Patent
Han et al.

(10) Patent No.: US 10,973,964 B2
(45) Date of Patent: Apr. 13, 2021

(54) MEDICAL ASPIRATOR HAVING CONSTANT SUCTION PRESSURE

(71) Applicant: INDUSTRY-UNIVERSITY COOPERATION FOUNDATION HANYANG UNIVERSITY, Seoul (KR)

(72) Inventors: Seog Young Han, Seoul (KR); Dae Hwan Moon, Seoul (KR)

(73) Assignees: INDUSTRY-UNIVERSITY COOPERATION, Seoul (KR); FOUNDATION HANYANG UNIVERSITY, Seoul (KR)

( * ) Notice: Subject to any disclaimer, the term of this patent is extended or adjusted under 35 U.S.C. 154(b) by 321 days.

(21) Appl. No.: 15/775,208

(22) PCT Filed: Nov. 11, 2016

(86) PCT No.: PCT/KR2016/013030
§ 371 (c)(1),
(2) Date: May 10, 2018

(87) PCT Pub. No.: WO2017/082689
PCT Pub. Date: May 18, 2017

(65) Prior Publication Data
US 2018/0353660 A1 Dec. 13, 2018

(30) Foreign Application Priority Data

Nov. 11, 2015 (KR) .................. 10-2015-0158308
Nov. 11, 2015 (KR) .................. 10-2015-0158311

(51) Int. Cl.
*A61M 1/00* (2006.01)
*A61M 35/00* (2006.01)
(Continued)

(52) U.S. Cl.
CPC .......... *A61M 1/0031* (2013.01); *A61M 1/007* (2014.02); *A61M 1/0009* (2013.01);
(Continued)

(58) Field of Classification Search
CPC .......... A61M 1/00; A61M 35/00; A61M 5/00; A61M 29/00; A61M 27/00
See application file for complete search history.

(56) References Cited

U.S. PATENT DOCUMENTS 2,904,044 A * 9/1959 Jalar ................. A61M 5/24
604/228
8,177,764 B2 5/2012 Hu et al.
(Continued)

FOREIGN PATENT DOCUMENTS

JP     2004-016469 A     1/2004
JP     2006242278 A *    3/2005
KR   10-2013-0078346 A   7/2013

*Primary Examiner* — Tatyana Zalukaeva
*Assistant Examiner* — Ilya Y Treyger
(74) *Attorney, Agent, or Firm* — Novick, Kim & Lee, PLLC; Sang Ho Lee

(57) ABSTRACT

Provided is a medical aspirator including a hollow cylinder housing having a space therein, a piston slidable inside the cylinder housing in a longitudinal direction, and an elastic member having one end connected to the piston and the other end fixed to the cylinder housing, and allowing the piston to move in the longitudinal direction with a constant force, in which after the medical aspirator is installed in a surgical site, a constant suction pressure is maintained, so that side effects and accidents such as organ adhesion and tissue damage in a surgical site, resulting from an excessive pressure, are reduced, and body fluid in the surgical site is effectively discharged, so that the medical aspirator may contribute to shortening of a recovery period of a patient. Further, the present disclosure relates to a medical aspirator including an upper housing constituting an upper body, a (Continued)

lower housing constituting a lower body, a sealing film coupled along outer surfaces of the upper housing and the lower housing and having a space formed in the sealing film, and a screw thread connector connecting the upper housing and the lower housing and having a screw thread, in which after the medical aspirator is installed in a surgical site, a constant suction pressure is maintained, so that side effects and accidents such as organ adhesion and tissue damage in a surgical site, resulting from an excessive pressure, are reduced, and body fluid in the surgical site is effectively discharged, so that the medical aspirator may contribute to shortening of a recovery period of a patient.

13 Claims, 17 Drawing Sheets

(51) Int. Cl.
  *A61M 5/00* (2006.01)
  *A61M 29/00* (2006.01)
  *A61M 27/00* (2006.01)

(52) U.S. Cl.
  CPC ........ *A61M 1/0011* (2013.01); *A61M 1/0068* (2014.02); *A61M 1/0001* (2013.01); *A61M 1/0088* (2013.01)

(56) References Cited

U.S. PATENT DOCUMENTS

| | | | |
|---|---|---|---|
| 8,858,516 B2 | 10/2014 | Hu et al. | |
| 9,744,275 B2 * | 8/2017 | Khouri | A61M 1/0009 |
| 2001/0047158 A1 | 11/2001 | Ladd | |
| 2002/0022854 A1 | 2/2002 | Irion et al. | |

* cited by examiner

MEDICAL ASPIRATOR HAVING CONSTANT SUCTION PRESSURE

TECHNICAL FIELD

The present disclosure relates to a medical aspirator, and more particularly, to a device used in a hospital and a medical equipment field related to a recovery process after a surgery, and configured to discharge blood or exudate generated in a surgical site.

BACKGROUND ART

Blood, exudate, and body fluid are collected in tissues after a surgical operation, and the collected blood and the collected exudate disturb healing of injuries, thereby causing complications.

Thus, a medical aspirator such as Hemovac and Barovac is used to prevent the blood and the exudate from being collected after a surgery.

Such a medical aspirator may be used in a hospital and a medical equipment field mainly related to a recovery process after a surgery, and may be applied even to a negative pressure injury treatment device using the same principle.

FIG. 1 is a perspective view illustrating a medical aspirator according to the related art, and FIG. 2 is a front view illustrating the medical aspirator according to the related art.

Referring to FIG. 1, the medical aspirator according to the related art generally includes a bottom plate 10, a pressure plate 20 spaced apart from the bottom plate 10, connected to a liquid drainage tube 21, and having a discharge hole 22 provided with a cap 23, a coil spring 30 installed between the bottom plate 10 and the pressure plate 20, and a sealing film 40 connecting the edges of the bottom plate 10 and the pressure plate 20 to form a space between the bottom plate 10 and the pressure plate 20, in which body fluid may be accommodated.

However, in the above-described medical aspirator according to the related art, an additional operation is required in which while the pressure plate is pushed from the upper side to the lower side to extract body fluid such as blood and exudate, the cap is closed to seal the discharge hole. In this case, there is a problem in that a lot of power is required to allow nurses, who are mostly women, to use the medical aspirator.

Further, in a state in which the pressure plate is lifted up to a specific height since the nurses fail to overcome elasticity of the coil spring 30 after pushing the pressure plate, when the discharge hole 22 is sealed by the cap 23, the body fluid of a human body is stored in a space inside the sealing film 40 in a state in which external air is introduced into the airtight film 40. In this case, there is a problem in that the body fluid of the human body may be polluted by the external air.

FIG. 3 is a graph depicting a change in a pressure according to a suction time of the medical aspirator according to the related art.

As illustrated, in the medical aspirator according to the related art, although a suction pressure is strong due to a compressed spring in an initial stage of mounting, the suction pressure is gradually weakened as the spring is restored by lapse of time.

Accordingly, when suction starts, the suction pressure is too strong, and thus a surgical site tissue may be injured or stenosed by a suction tube. Further, at an end of the suction, the suction pressure is too weak, and thus the blood or the exudate may not be properly discharged.

Japanese Patent Laid-Open Publication No. 2004-016469 entitled "medical discharge tool" (published on Jan. 22, 2004) is disclosed as the related prior art.

DISCLOSURE

Technical Problem

To solve the above-described problems, the present disclosure provides a medical aspirator in which after the medical aspirator is installed in a surgical site, a constant suction pressure is maintained, so that side effects such as organ adhesion and tissue damage in a surgical site, resulting from an excessive pressure, are reduced, and body fluid in the surgical site is effectively discharged, so that the medical aspirator may contribute to shortening of a recovery period of a patient.

Further, the present disclosure also provides a device that may be applied even to a negative pressure wound treatment device using the same principle.

Technical Solution

To achieve the above-described objects, a medical aspirator having a constant suction pressure according to an embodiment of the present disclosure may include a hollow cylinder housing having a space formed in the cylinder housing, a piston slidable inside the cylinder housing in a longitudinal direction, and an elastic member having one end connected to the piston and the other end fixed to the cylinder housing, and allowing the piston to move in the longitudinal direction with a constant force.

Further, according to the embodiment of the present disclosure, the elastic member may be a constant force spring.

Further, according to the embodiment of the present disclosure, the constant force spring includes a wound end and a fixed end.

Further, according to the embodiment of the present disclosure, a holder configured to fix the wound end may be mounted on one end of the cylinder housing.

Further, according to the embodiment of the present disclosure, an outer surface of the cylinder housing may include a hollow, and a stopper having a distal end protruding toward the space of the cylinder housing and having a rotational force such that the protruding distal end is rotated toward an outside of the hollow may be mounted on the hollow.

Further, according to the embodiment of the present disclosure, the cylinder housing may include a guide rail connected to the hollow on an outer surface of the cylinder housing and extending in the longitudinal direction, and a switch which is slid in the longitudinal direction to determine whether the stopper is rotated may be mounted on the guide rail.

To achieve the above-described objects, a medical aspirator having a constant suction pressure according to an embodiment of the present disclosure may include an upper housing constituting an upper body, a lower housing constituting a lower body, a sealing film coupled along outer surfaces of the upper housing and the lower housing and having a space formed in the sealing film, and a screw thread connector connecting the upper housing and the lower housing and having a screw thread.

Further, according to the embodiment of the present disclosure, the sealing film may have a corrugated shape.

Further, according to the embodiment of the present disclosure, a coil spring may be mounted on an outer circumferential surface of the screw thread connector.

Further, according to the embodiment of the present disclosure, the screw thread connector may include an outer screw thread connector coupled to the upper housing, and an inner screw thread connector coupled to the lower housing and inserted into the outer screw thread connector.

Further, according to the embodiment of the present disclosure, screw threads having shapes complementary to each other may be formed inside the outer screw thread connector and outside the inner screw thread connector, and the screw threads may be nonlinear screw threads.

Further, according to the embodiment of the present disclosure, a tangent slope of the screw threads may increase as the screw threads go toward the upper housing.

Further, according to the embodiment of the present disclosure, the upper housing and the lower housing may have a disc shape, and the screw thread connector may connect centers of the upper housing and the lower housing.

Further, according to the embodiment of the present disclosure, the upper housing and the lower housing may have a rod shape, a length of which is longer than a width, and the screw thread connector may connect ends of the upper housing and the lower housing.

Further, according to the embodiment of the present disclosure, the upper housing may be rotated with respect to the lower housing as the coil spring is expanded, and the sealing film may be unfolded in a fan shape.

Advantageous Effects

According to the present disclosure, a negative pressure of a medical aspirator is stably generated, so that side effects and accidents such as organ adhesion and tissue damage in a surgical site, resulting from an excessive pressure, are reduced, and since the negative pressure is stably generated, body fluid in a surgical site is effectively discharged, so that a recovery period of a patient is shortened and pain is reduced.

Further, according to the present disclosure, since the medical aspirator has a simple structure and is easily manufactured, excellent productivity is achieved. Even on an economic aspect, the medical aspirator may be applied to all the existing aspirator products, and similar products may be designed, so that there is a high possibility that an application field will expand.

DESCRIPTION OF MAIN REFERENCE NUMERALS OF DRAWINGS

Figure 1:
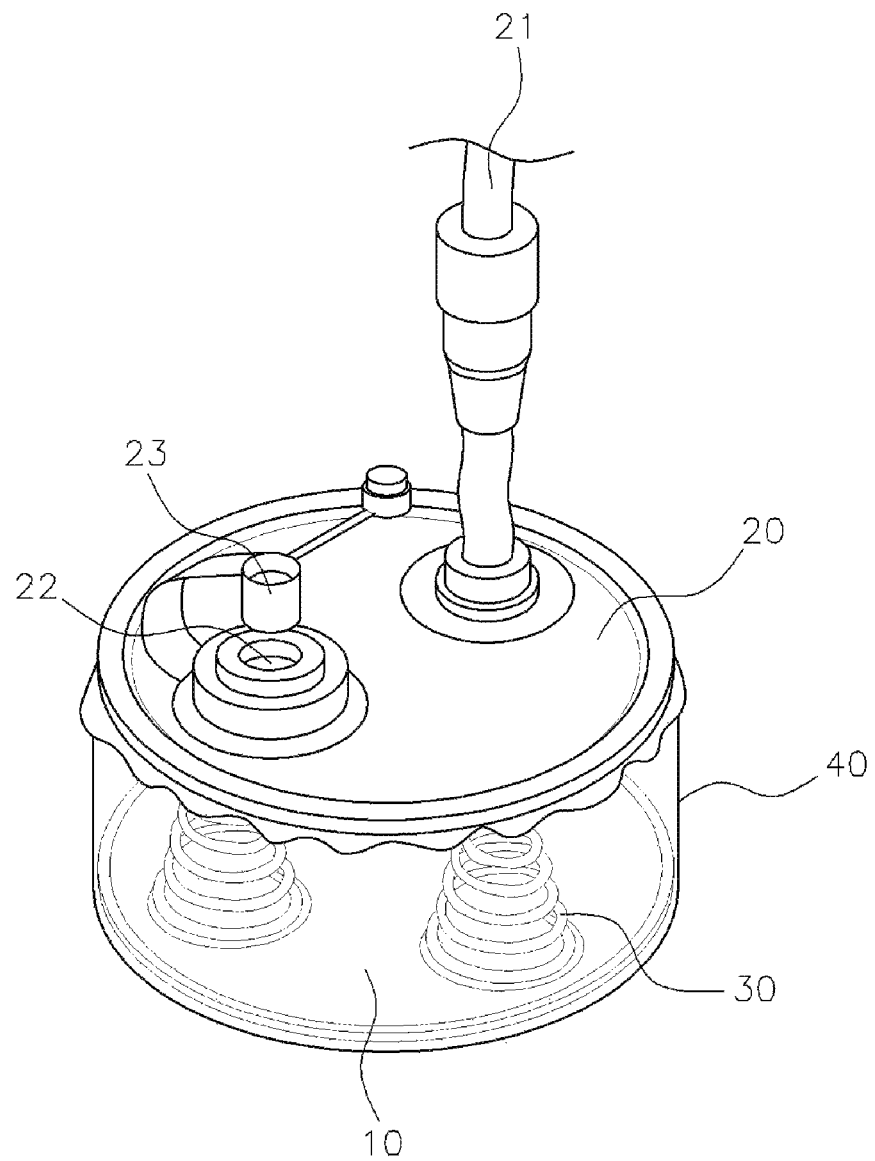
FIG. 1 is a perspective view illustrating a medical aspirator according to the related art.
Figure 2:
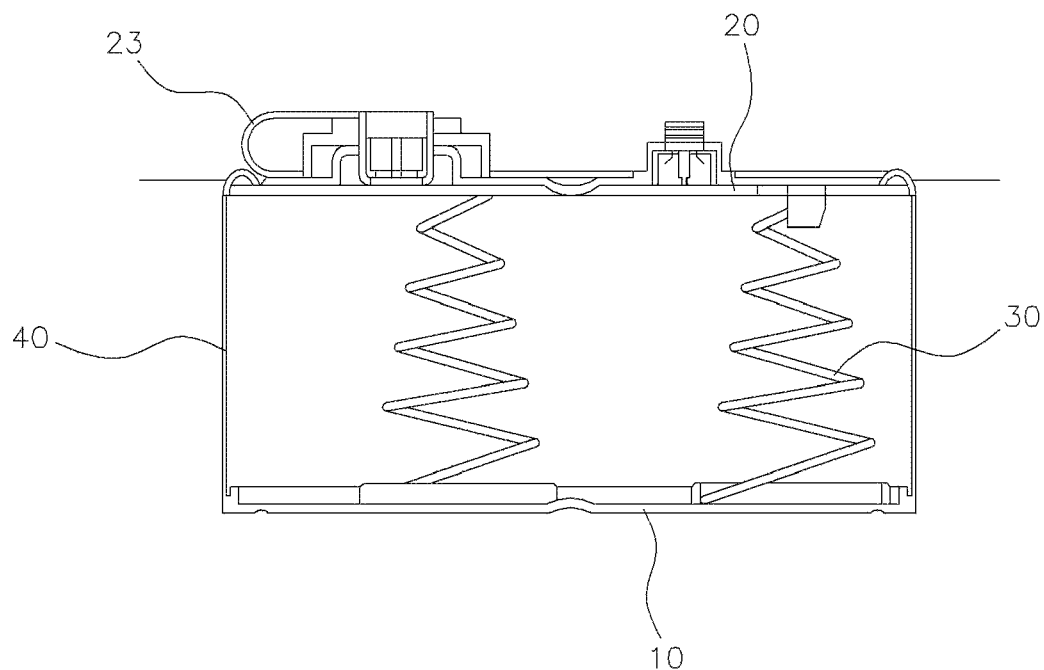
FIG. 2 is a front view illustrating the medical aspirator according to the related art.
Figure 3:
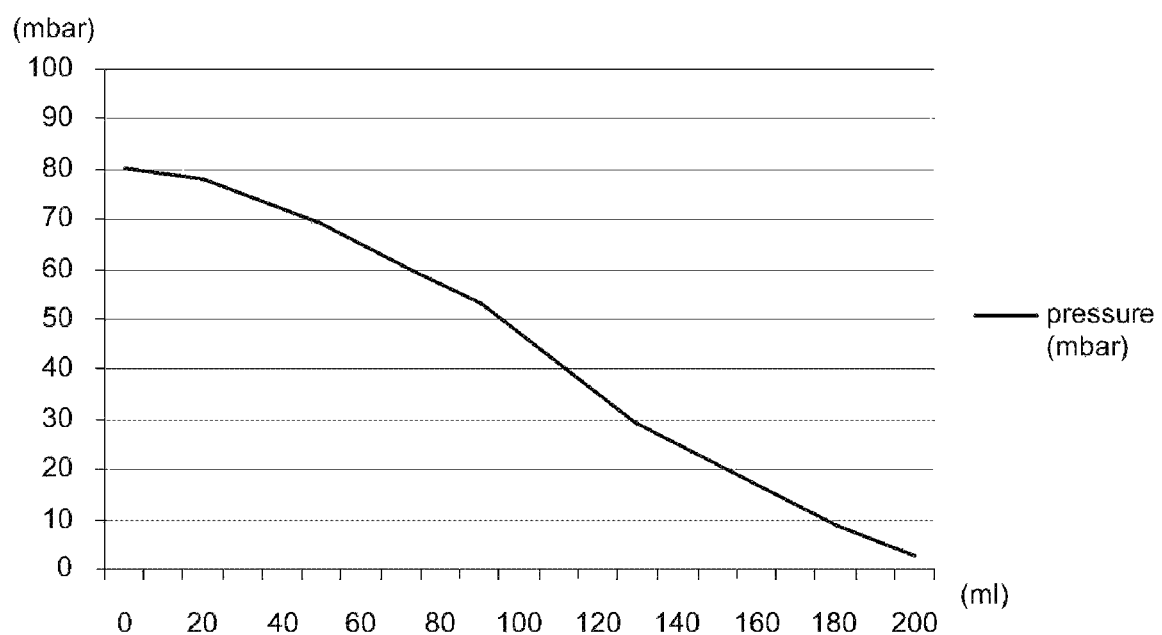
FIG. 3 is a graph depicting a change in a pressure according to a suction time of the general medical aspirator according to the related art.

10: Bottom plate
20: Pressure plate
21: Liquid drainage tube
22: Discharge hole
23: Cap
30: Coil spring
40: Sealing film
50: Suction port
60: Drainage tube
70: Trocar
80: Exudate
100: Cylinder housing
101: Space
110: Opening
120: Hollow
130: Guide rail
140: Pin hole
200: Piston 210: Piston ring
300: Constant force spring
301: Wound end
302: Fixed end
310: Holder
400: Stopper
410: Switch
420: Safety pin
510: Upper housing
520: Lower housing
530: Screw thread connector
531: Outer screw thread connector
532: Inner screw thread connector
533: Linear screw thread
534: Nonlinear screw thread Best Mode Hereinafter, embodiments of the present disclosure will be described in detail with reference to the accompanying drawings. The embodiments which will be described below are provided as an example such that those skilled in the art to which the present disclosure pertains may fully understand the spirit of the present disclosure. The present disclosure is not limited to the embodiments which will be described below, and may be embodied in other forms.

A part unrelated to the description is omitted to clearly describe the present disclosure, and in the drawings, the widths, the lengths, the thicknesses, and the like of components may be exaggeratedly expressed for convenience. Throughout the specification, the same components are designated by the same reference numerals.

Figure 4:
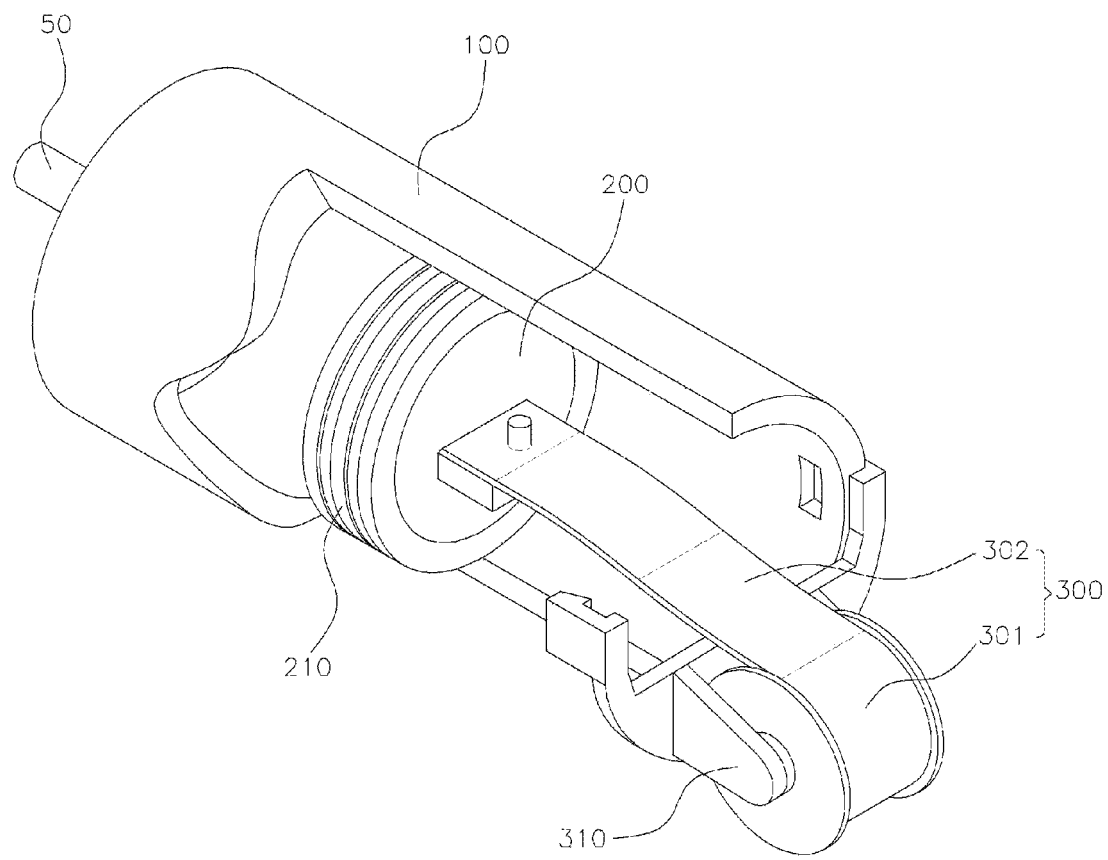
FIG. 4 is a partial transparent perspective view illustrating a medical aspirator according to an embodiment of the present disclosure.
Figure 5:
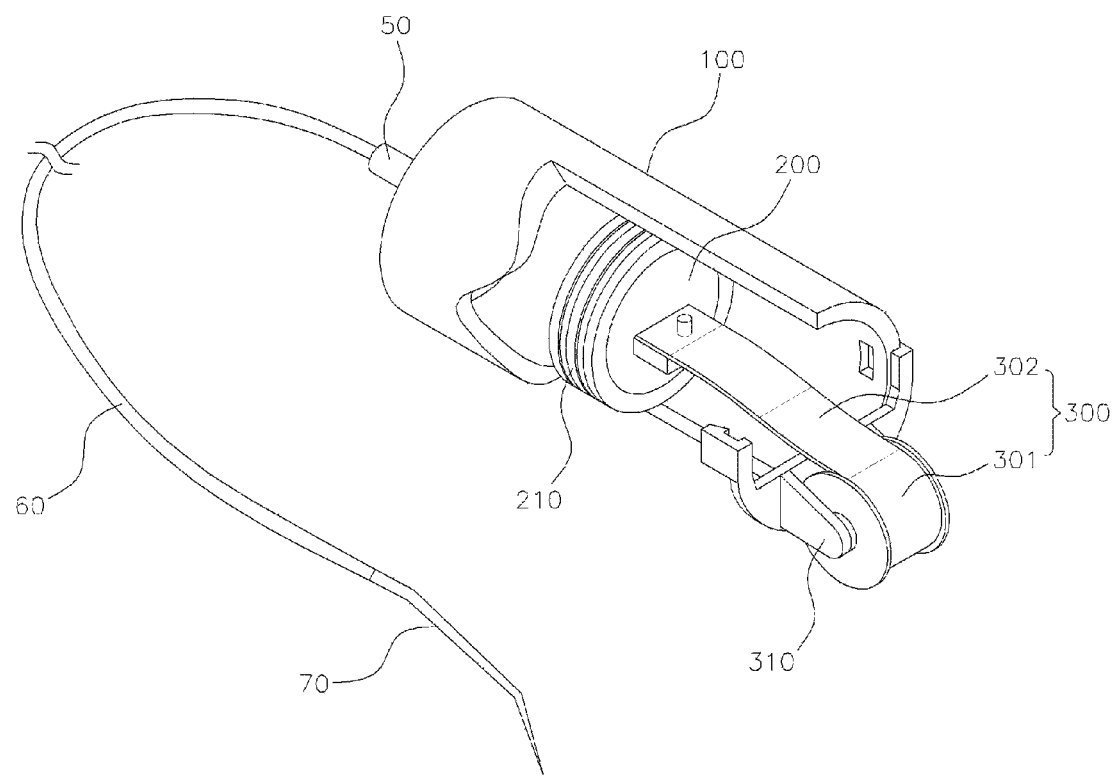
FIG. 5 is a utilization diagram illustrating the medical aspirator according to the embodiment of the present disclosure.

FIG. 4 is a partial transparent perspective view illustrating a medical aspirator according to an embodiment of the present disclosure, and FIG. 5 is a utilization diagram illustrating the medical aspirator according to the embodiment of the present disclosure. It is apparent that the present disclosure is not limited thereto, and other devices using an aspirator may be derived through change and modification by those skilled in the art.

Figure 6A:
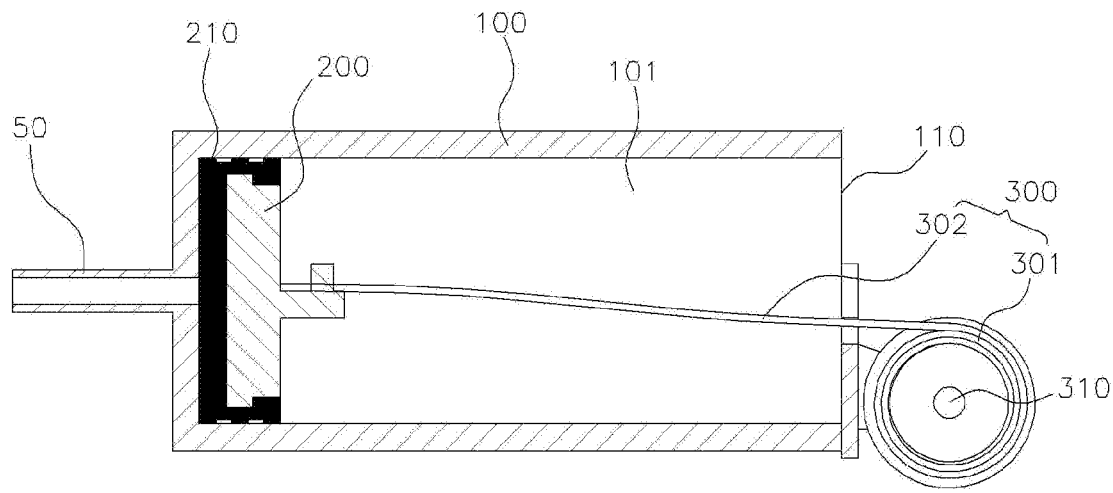
FIG. 6A is a sectional view illustrating the medical aspirator according to the embodiment of the present disclosure before operation.
Figure 6B:
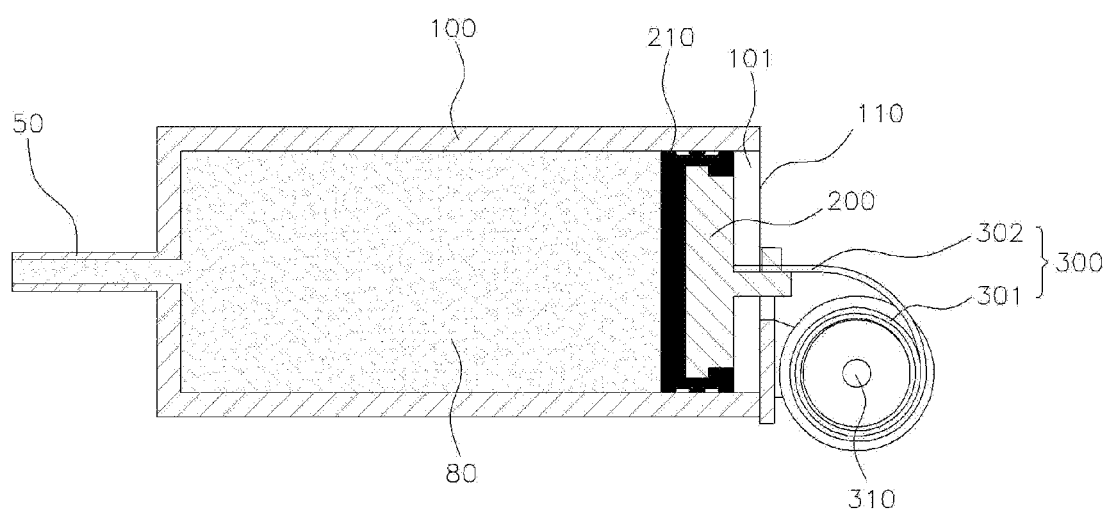
FIG. 6B is a sectional view illustrating the medical aspirator according to the embodiment of the present disclosure after operation.

FIG. 6A is a sectional view illustrating the medical aspirator according to the embodiment of the present disclosure before operation, and FIG. 6B is a sectional view illustrating the medical aspirator according to the embodiment of the present disclosure after operation.

Referring to the above drawings, the medical aspirator according to the embodiment of the present disclosure relates to an aspirator for maintaining a constant suction pressure, which includes a hollow cylinder housing 100, a piston 200, an elastic member, and the like, to implement the same.

The cylinder housing 100, which is a hollow body, has a cylindrical space 101 having a circular cross section, and the piston 200 and the elastic member are provided in the cylinder housing 100 side by side to be slidable along a longitudinal direction of the space 101.

Hereinafter, description will be made while a longitudinal direction is defined as a direction that is perpendicular to the circular cross section of the cylindrical housing 100, which corresponds to a left-right direction of FIGS. 6A and 6B.

The piston 200 has a circular cross section that is perpendicular to the longitudinal direction, has a predetermined thickness, and is slidable inside the cylinder housing 100 along the longitudinal direction.

The elastic member, which corresponds to a kind of piston rod fixedly connected to the piston 200 to enable sliding of the piston 200, has one end connected to the piston 200 and the other end fixed to the cylinder housing 100.

Figure 7:
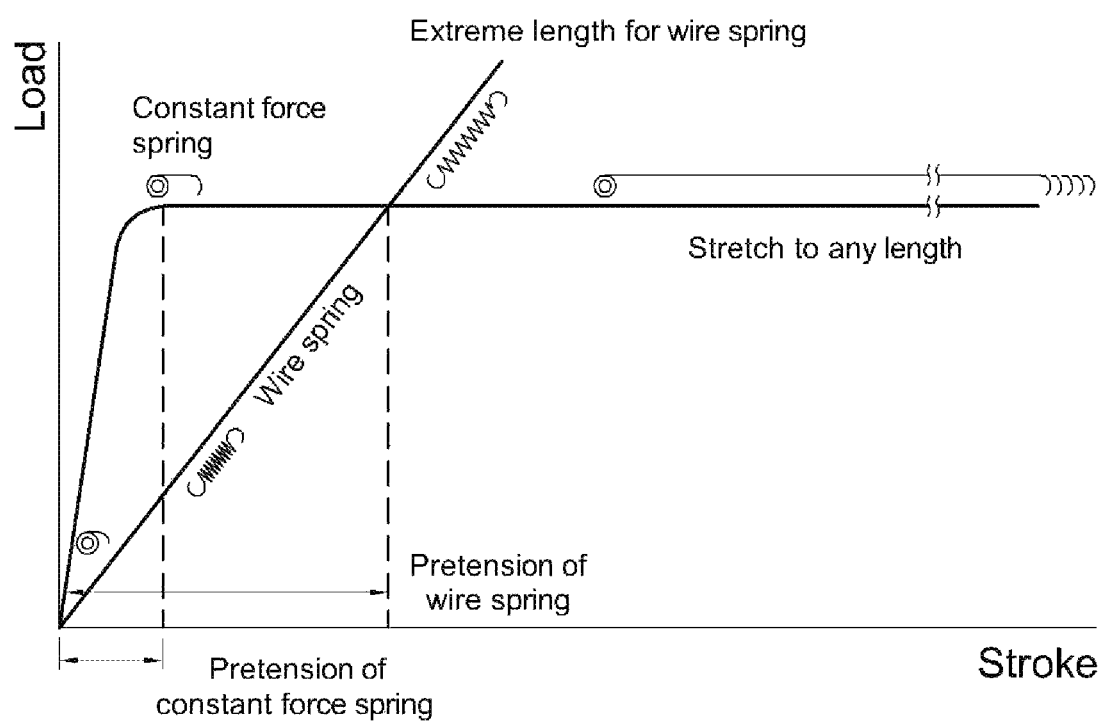
FIG. 7 is a graph depicting a relationship between a stroke and a load according to the type of elastic member.

FIG. 7 is a graph depicting a relationship between a stroke and a load according to the type of elastic member.

Referring to FIG. 7, in a typical wire spring, a load increases together as a stroke increases. However, in the elastic member according to the present disclosure, after a specific time point, the load is constant regardless of the stroke.

The elastic member according to the present disclosure is connected to the piston 200 such that the piston 200 may be slid in the longitudinal direction with a specific force.

Through this, the medical aspirator according to the present disclosure may generate a constant suction pressure from a starting time point to an end time point of suction.

It is preferable that the elastic member according to the present disclosure, which is a plate-shaped spring bent at a specific curvature, is a constant force spring 300 in which a load generated when the constant force spring 300 is stretched is constant regardless of a stroke.

In general, since the constant force spring 300 has the load only in one direction, in the present embodiment, the constant force spring 300 has one end connected to the piston 200 and the other end fixed to the cylinder housing 100 so that the piston 200 is slid at a constant load regardless of the stroke, and accordingly, a constant suction pressure may be maintained.

Although description will be made below based on the medical aspirator to which the constant force spring 300 is applied, the constant force spring 300 may include all elastic members for allowing the piston 200 to move with a constant force in the longitudinal direction.

The constant force spring 300 may include a wound end 301 and a fixed end 302. The fixed end 302 may be connected to the piston 200 through catching and fixing, and the wound end 301 may be fixed by a holder 310 mounted on one end of the cylinder housing 100.

The wound end 301 has a hollow coil shape, and the holder 310 may pass through a central portion of the wound end 301 to fix the constant force spring 300.

When the wound end 301 is rotated, the length of the fixed end 302 may be reduced, the constant force spring 300 may be compressed, and the piston 200 connected to the fixed end 302 may be slid toward the wound end 301 fixed to the cylinder housing 100 in the longitudinal direction.

A piston ring 210 mounted along an outer circumferential surface of the piston 200 and formed of an elastic material may be mounted on the piston 200, and a gap between the piston 200 and the cylinder housing 100 is sealed, so that air or exudate 80 may be prevented from leaking, and the suction pressure may be maintained.

A process of operating the medical aspirator according to the embodiment of the present disclosure will be described below.

Referring to FIG. 6A, the constant force spring 300 is expanded to the maximum so that the piston 200 comes into contact with the other end of the cylinder housing 100.

An opening 110 configured to press the piston 200 from the outside to slide the piston 200 may be formed at the one end of the cylinder housing 100.

For example, as a user inserts his/her hand through the opening 110 to press one surface of the piston, the other surface of the piston 200 may come into contact with an inner surface of the cylinder housing 100.

In this case, a suction port 50 may be closed by the piston 200 or the piston ring 210, and may prevent the exudate 80 from being introduced into the cylinder housing 100.

The user may directly fix the piston 200 using his/her body, or may fix the piston 200 using a separate fixing means as described below.

Referring to FIG. 6B, when the piston 200 is unfixed, the constant force spring 300 is compressed to slide the piston 200 in the longitudinal direction.

As the piston 200 is slid, when the suction port 50 closed by the piston 200 or the piston ring 210 is open, the exudate 80 is introduced into the cylinder housing 100 from a drainage tube 60, a trocar 70, or the like connected to the suction port 50. In this process, the suction pressure is maintained constant according to characteristics of the elastic member according to the present disclosure.

Figure 8A:
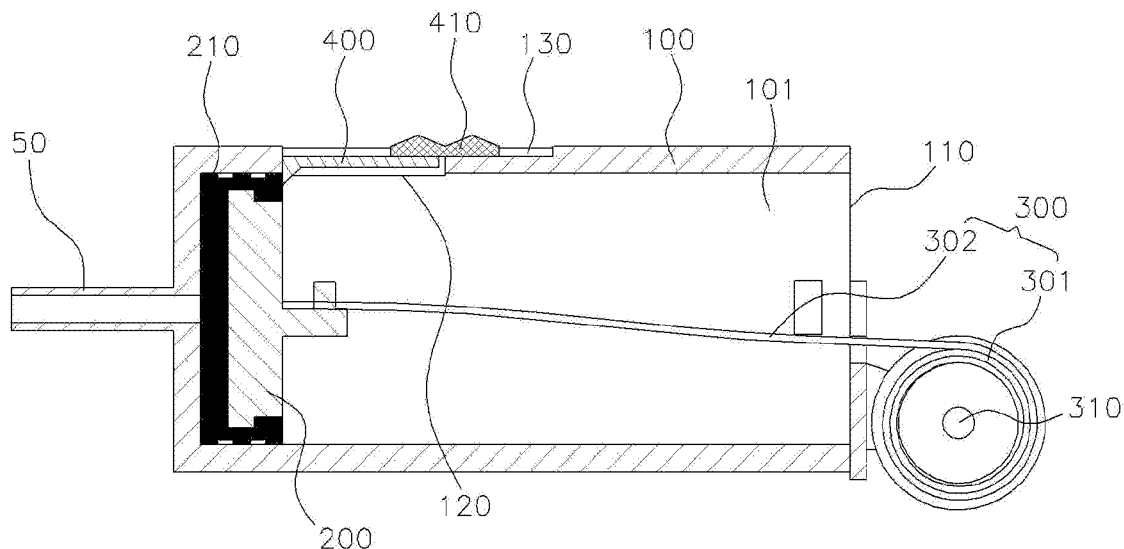
FIG. 8A is a sectional view illustrating the medical aspirator on which a stopper is mounted according to the embodiment of the present disclosure before the medical aspirator is unfixed.
Figure 8B:
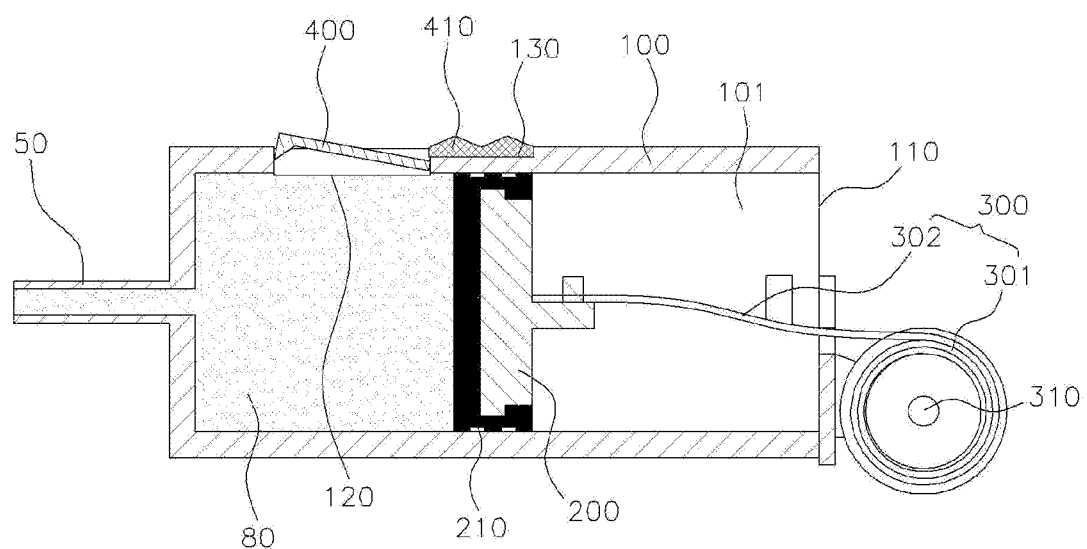
FIG. 8B is a sectional view illustrating the medical aspirator on which the stopper is mounted according to the embodiment of the present disclosure after the medical aspirator is unfixed.

FIG. 8A is a sectional view illustrating the medical aspirator on which a stopper is mounted according to the embodiment of the present disclosure before the medical aspirator is unfixed, and FIG. 8B is a sectional view illustrating the medical aspirator on which the stopper is mounted according to the embodiment of the present disclosure after the medical aspirator is unfixed.

Referring to FIGS. 8A and 8B, the cylinder housing 100 may include a hollow 120 configured to mount a stopper 400 on the outer surface thereof.

The stopper 400, which is a device configured to fix the piston 200 against a compressive force of the constant force spring 300 when the constant force spring 300 is expanded to the maximum, may protrude toward the space 101 of the cylinder housing 100 such that the piston 200 is caught and fixed by a distal end thereof.

That is, as a protruding part of the stopper 400 supports one surface of the piston 200, the constant force spring 300 may be prevented from being compressed.

A protruding distal end may basically have a rotation force for rotation in an outward direction of the hollow 120. To this end, a member (not illustrated) such as a spring and a wire may be additionally mounted.

Thus, the stopper 400 may be rotated at a predetermined angle in an outward direction of the hollow 120, and accordingly, the protruding distal end of the stopper 400 is lifted up so that the piston 200 may be uncaught and unfixed.

The cylinder housing 100 may include a guide rail 130 connected to the hollow 120 on the outer surface thereof and extending in the longitudinal direction. A switch 410 slid in the longitudinal direction to determine whether the stopper 400 is rotated may be mounted on the guide rail 130.

A process of operating the medical aspirator according to the embodiment of the present disclosure, on which a fixing means for the piston 200 is mounted, will be described below.

Referring to FIG. 8A, the constant force spring 300 is expanded to the maximum so that the piston 200 comes into contact with the inner surface of the cylinder housing 100.

One surface of the protruding part of the stopper 400 is perpendicular to the longitudinal direction of the cylinder housing 100 and the other surface of the protruding part of the stopper 400 is inclined in an opposite direction.

As the distal end of the stopper 400 has the above-described asymmetrical shape, it is easy that the piston 200 passes through the stopper 400 to be slid toward the suction port 50. However, after passing through the stopper 400, the piston 200 may be suppressed from being moved in an opposite direction by the stopper 400, and thus may be fixed.

The switch 410 mounted on the guide rail 130 may be located on the outer surface of the stopper 400 to prevent the stopper 400 from being rotated in an outward direction of the hollow 120.

Referring to FIG. 8B, in order to operate the aspirator, the switch 410 is slid along the guide rail 130 in the longitudinal direction, and the protruding part of the stopper 400 is rotated in an outward direction of the cylinder housing 100 by a predetermined angle by a rotational force, so that the piston 200 is uncaught and unfixed.

Although it is illustrated in the drawing that the stopper 400 is rotated to unfix the piston 200, the stopper 400 is vertically lifted up to unfix the piston 200, and rotational movement and vertical movement of the stopper 400 may be complexly performed.

Such structures of the stopper 400 and the switch 410 correspond to an example, and the present disclosure is not limited thereto.

Figure 9A:
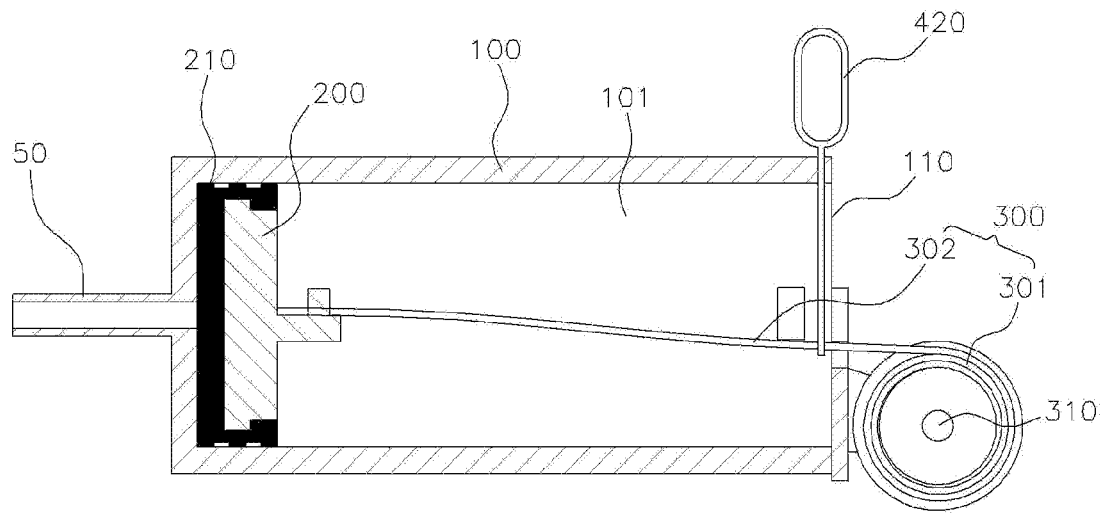
FIG. 9A is a sectional view illustrating the medical aspirator on which a safety pin is mounted according to the embodiment of the present disclosure before the medical aspirator is unfixed.
Figure 9B:
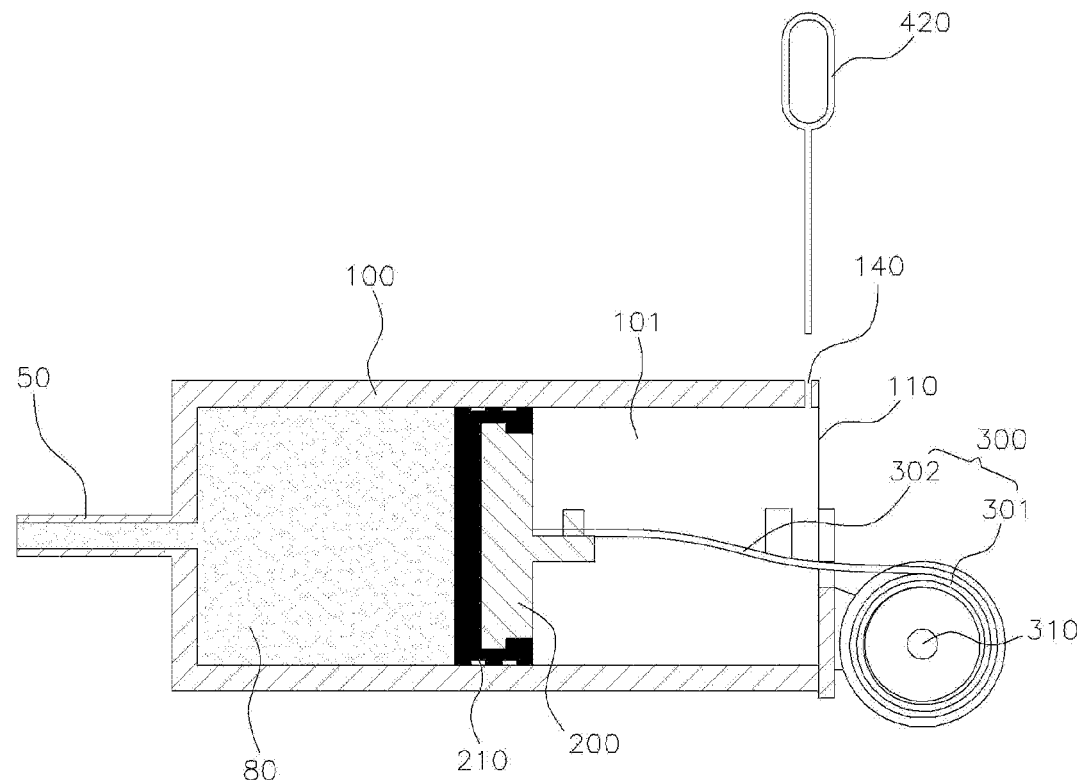
FIG. 9B is a sectional view illustrating the medical aspirator on which the safety pin is mounted according to the embodiment of the present disclosure after the medical aspirator is unfixed.

FIG. 9A is a sectional view illustrating the medical aspirator on which a safety pin is mounted according to the embodiment of the present disclosure before the medical aspirator is unfixed, and FIG. 9B is a sectional view illustrating the medical aspirator on which the safety pin is mounted according to the embodiment of the present disclosure after the medical aspirator is unfixed.

Referring to FIGS. 9A and 9B, the elastic member may include a fixing hole (not illustrated), and a safety pin 420 inserted from the outside of the cylinder housing 100 and configured to catch and fix the piston 200 may be mounted on the fixing hole.

In this case, a pin hole 140 through which the safety pin 420 is inserted may be additionally formed on an outer surface of the cylinder housing 100.

A process of operating the medical aspirator according to the embodiment of the present disclosure, on which the safety pin 420 is mounted, will be described below.

Referring to FIG. 9A, the constant force spring 300 is expanded to the maximum so that the piston 200 comes into contact with the other end of the cylinder housing 100. Next, the safety pin 420 is inserted through the pin hole 140 and the fixing hole to catch and fix the piston 200.

Referring to FIG. 9B, in order to operate the aspirator, the safety pin 420 may be removed from the outside of the cylinder housing 100 to uncatch and unfix the piston 200, and the other suction process is the same as above.

Figure 10:
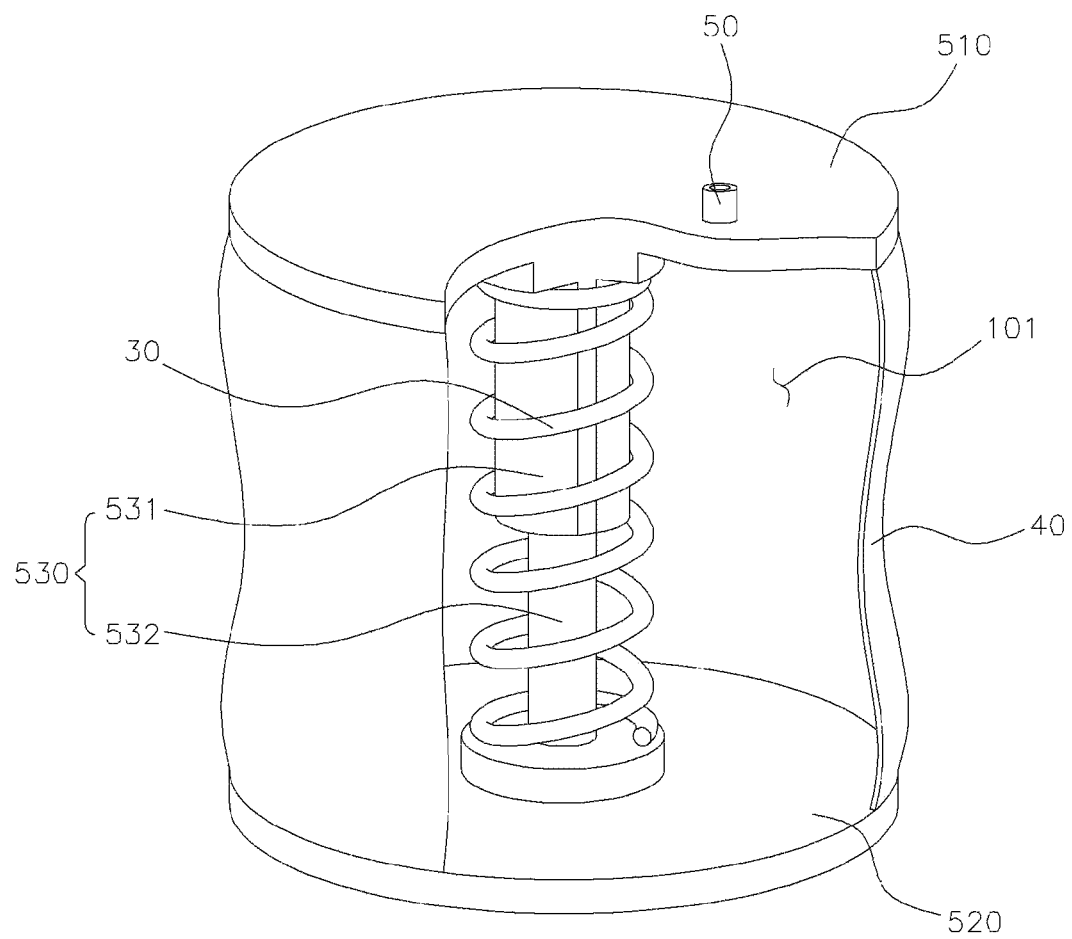
FIG. 10 is a partial transparent perspective view illustrating a medical aspirator according to another embodiment of the present disclosure.
Figure 11:
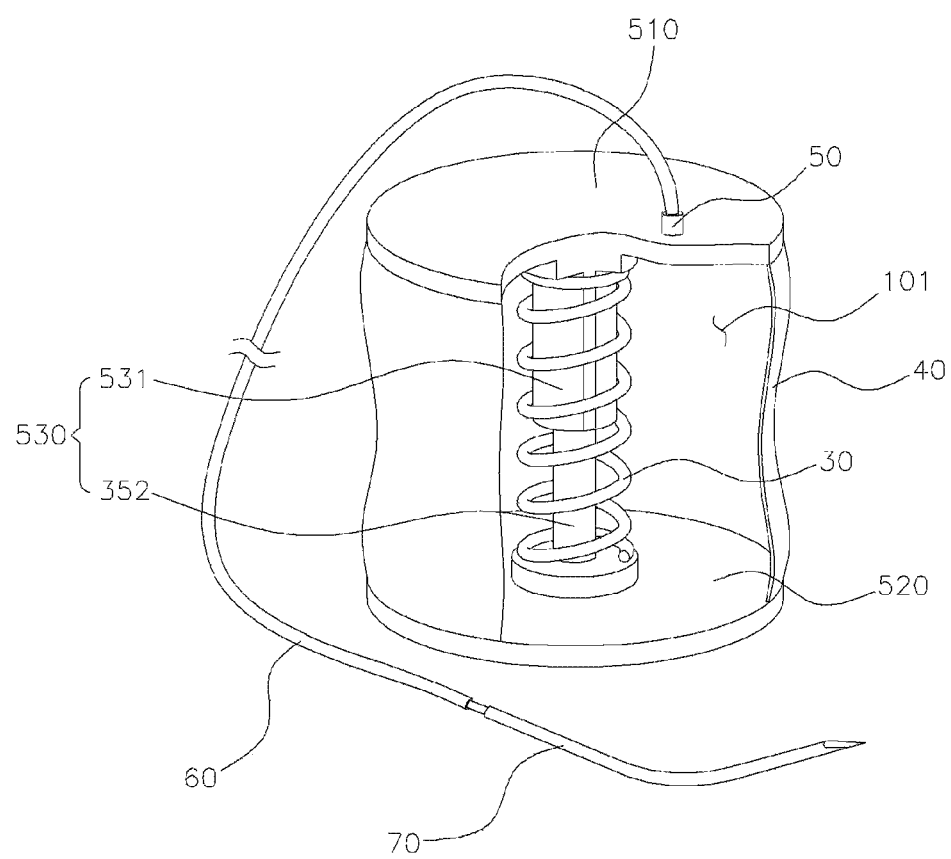
FIG. 11 is a utilization diagram illustrating the medical aspirator according to the another embodiment of the present disclosure.

FIG. 10 is a partial transparent perspective view illustrating a medical aspirator according to another embodiment of the present disclosure, and FIG. 11 is a utilization diagram illustrating the medical aspirator according to the another embodiment of the present disclosure. It is apparent that the present disclosure is not limited thereto, and other devices using an aspirator may be derived through change and modification by those skilled in the art.

Figure 12A:
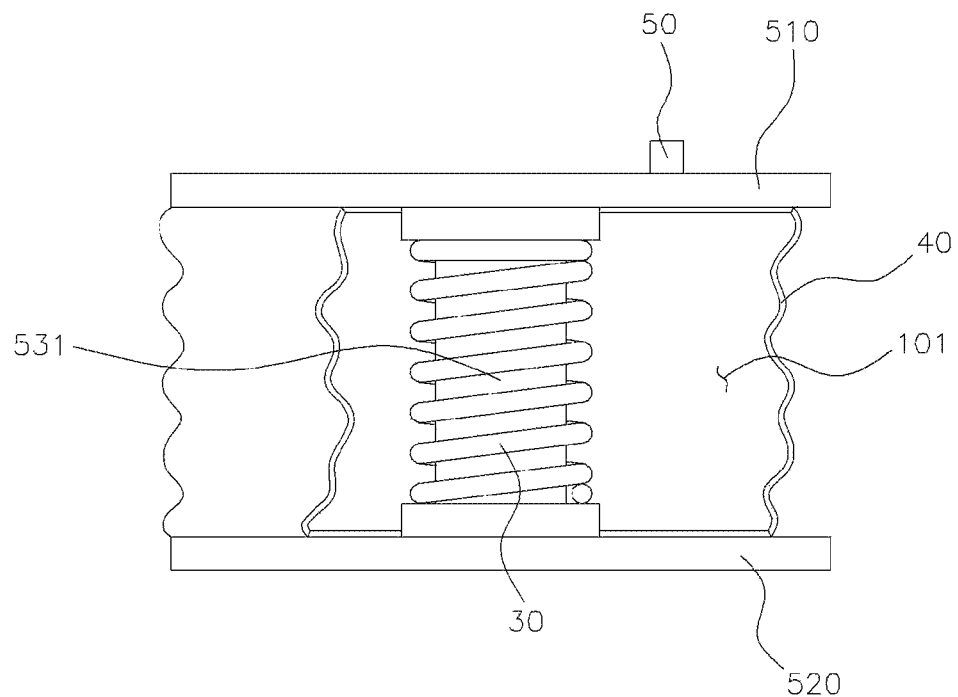
FIG. 12A is a partial transparent sectional view illustrating the medical aspirator according to the embodiment of the present disclosure before operation.
Figure 12B:
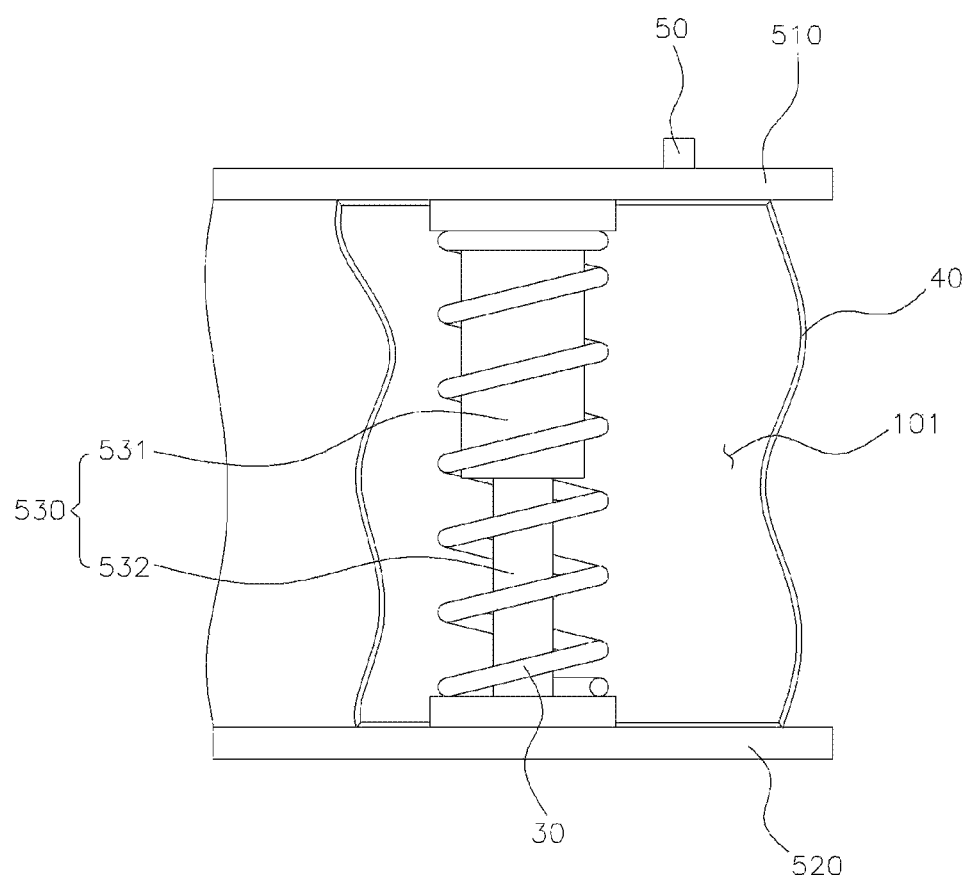
FIG. 12B is a partial transparent sectional view illustrating the medical aspirator according to the embodiment of the present disclosure after operation.

FIG. 12A is a partial transparent sectional view illustrating the medical aspirator according to the embodiment of the present disclosure before operation, and FIG. 12B is a partial transparent sectional view illustrating the medical aspirator according to the embodiment of the present disclosure after operation.

Referring to the above drawings, the medical aspirator according to the another embodiment of the present disclosure relates to an aspirator for maintaining a constant suction pressure, which includes an upper housing 510, a lower housing 520, a sealing film 40, a screw thread connector 530, a coil spring 30, and the like to implement the same.

The lower housing 520 may constitute a lower body of the medical aspirator, the upper housing 510 may constitute an upper body of the medical aspirator and may be pressed toward the lower housing 520.

It is preferable that the upper housing 510 and the lower housing 520 have the same shape. The sealing film 40 may be coupled along the outer surfaces of the upper housing 510 and the lower housing 520 so that a space 101 may be formed inside the upper housing 510 and the lower housing 520.

For example, the upper housing 510 and the lower housing 520 may have a disc shape, and the screw thread connector 530 may connect the centers of the upper housing 510 and the lower housing 520.

Hereinafter, description will be made while a height direction is defined as a direction which corresponds to a vertical direction of FIGS. 12A and 12B and is perpendicular to the upper housing 510 and the lower housing 520.

The screw thread connector 530 may connect the upper housing 510 and the lower housing 520 and may have screw threads formed therein, and a coil spring 30 may be mounted on the outer circumferential surface of the screw thread connector 530.

The coil spring 30 may be compressed or expanded in the height direction. Accordingly, the screw thread connector 530 may be also compressed or expanded together with the coil spring 30.

The screw thread connector 530 may include an outer screw thread connector 531 coupled to the upper housing 510 and an inner screw thread connector 532 coupled to the lower housing 520 and inserted into the outer screw thread connector 531.

The screw thread connector 530 may be formed integrally with the upper housing 510 and the lower housing 520 or may be fastened to the upper housing 510 and the lower housing 520 through a separate configuration.

In the medical aspirator according to the another embodiment of the present disclosure, a connector is configured by screw threads to escape characteristics of the existing linear spring.

Through this, an initial strong force of a spring is offset by a frictional force of the screw threads to prevent the suction pressure from becoming excessively strong when suction starts, so that the suction pressure may be maintained at a constant level.

Moreover, a vertical force used when the upper housing 510 is pressed is converted into a rotational force, so that nurses, who are mostly women in a medical field, may easily use the medical aspirator.

All structures used in the technical field, such as a ball screw and a screw thread similar thereto in addition to a structure of a bolt and a nut may be used for the screw threads.

The sealing film 40 may have a corrugated shape, and may be expanded together as the coil spring 30 is expanded, to increase the volume of the space 101 formed therein.

A process of operating the medical aspirator according to the another embodiment of the present disclosure will be described below.

Referring to FIG. 12A, the upper housing 510 is pressed toward the lower housing 520. In this process, the inner screw thread connector 532 is inserted into the outer screw thread connector 531 and the coil spring 30 is compressed.

After the coil spring 30 is compressed, a separate fixing means configured to fix the upper housing 510 and the lower housing 520, such as a clip, may be provided.

That is, before the aspirator is mounted, it is necessary to strongly fix the upper housing 510 and the lower housing 520 to suppress a force of expanding the coil spring 30.

Referring to FIG. 12B, as the fixing means is removed to operate the aspirator, the coil spring 30 is gradually expanded and the sealing film 40 having a corrugated shape is also expanded to increase the volume of the inner space 101. Accordingly, the exudate 80 is introduced through the suction port 50.

At this time, the initial strong force of the coil spring 30 is offset by a frictional force of the screw threads of the screw thread connector 530, so that the suction pressure may be maintained constant.

It is preferable that the screw threads may be formed inside the outer screw thread connector 531 and outside the inner screw thread connector 532, and may have shapes complementary to each other.

Figure 13A:
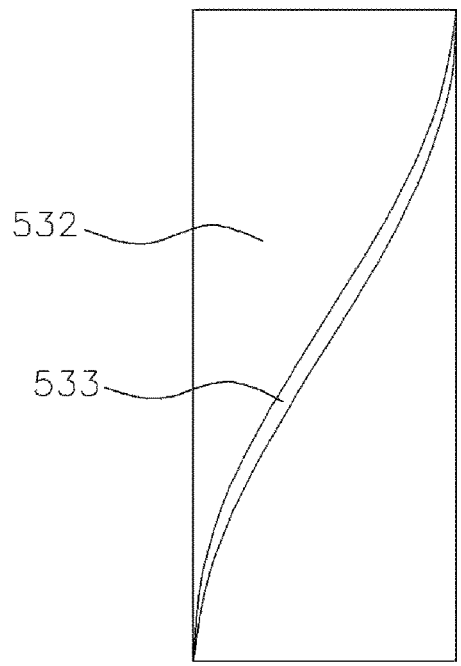
FIG. 13A is a front view illustrating a linear screw thread formed in an inner screw thread connector.
Figure 13B:
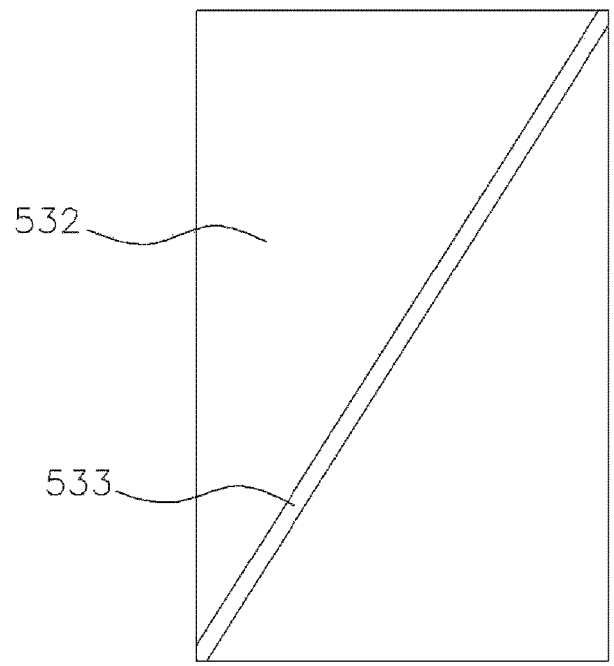
FIG. 13B is an exploded view illustrating the linear screw thread formed in the inner screw thread connector.
Figure 14A:
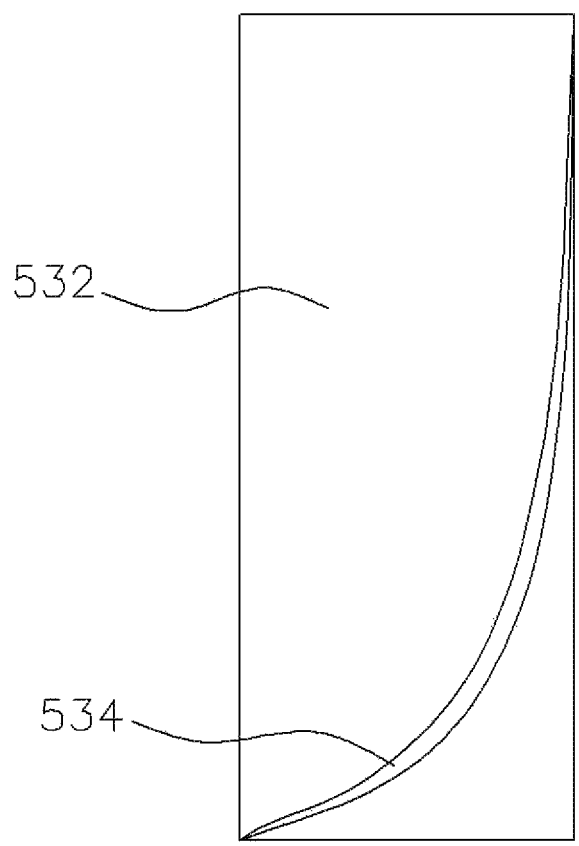
FIG. 14A is a front view illustrating a nonlinear screw thread formed in an inner screw thread connector.
Figure 14B:
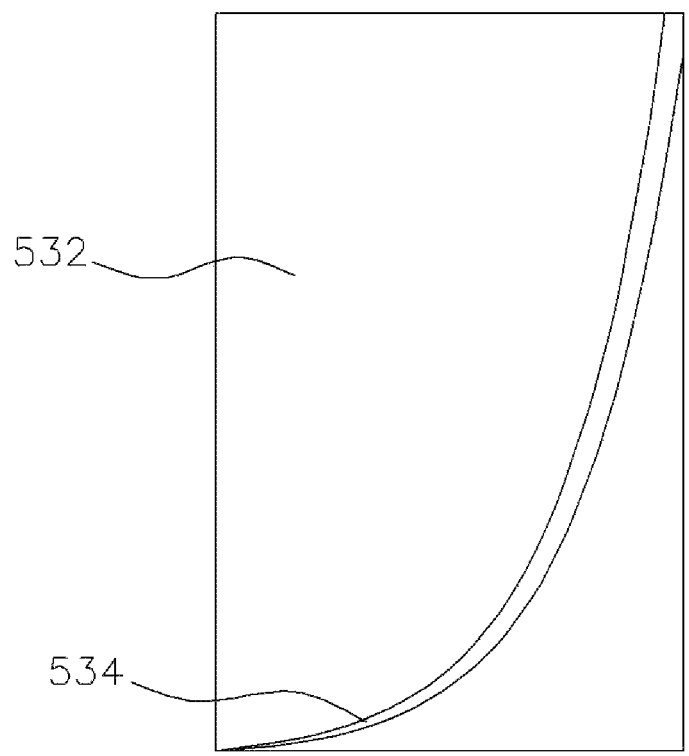
FIG. 14B is an exploded view illustrating the nonlinear screw thread formed in the inner screw thread connector.

FIG. 13A is a front view illustrating a linear screw thread formed in an inner screw thread connector, FIG. 13B is an exploded view illustrating the linear screw thread formed in the inner screw thread connector, FIG. 14A is a front view illustrating a nonlinear screw thread formed in an inner screw thread connector, and FIG. 14B is an exploded view illustrating the nonlinear screw thread formed in the inner screw thread connector.

Referring to the above drawings, the other configurations except for the inner screw thread connector 532 will be omitted to show the shape of the screw threads.

FIGS. 13A and 13B illustrate a linear screw thread 533. When an initial change in a pressure cannot be adjusted only by a frictional force and a slope of the screw thread, as a nonlinear screw thread 534 is implemented as illustrated in FIGS. 14A and 14B, a pressure variation rate may be adjusted to ultimately maintain the suction pressure at a certain level.

In this case, it is preferable that the screw thread is formed such that a tangent slope of the screw thread increases as the screw thread goes toward the upper housing 510.

Accordingly, in an initial time of mounting, an initial strong force of a spring may be suppressed by a strong frictional force of the screw thread having a small slope. The force of the spring, which is weakened as a time elapses, may be supplemented by a frictional force of the screw thread having a large slope. This is obtained in consideration of a sum of an expansion force of the coil spring 30 and the frictional force of the screw thread, and the suction pressure may be maintained more constant regardless of an operating time.

Figure 15A:
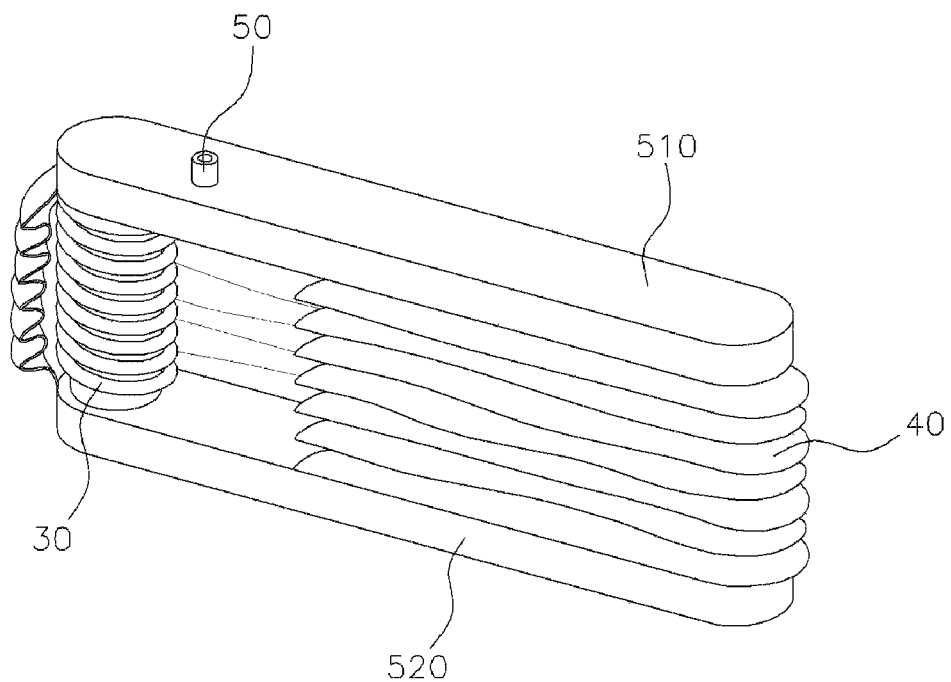
FIGS. 15A to 15C are views illustrating an operation process of a medical aspirator according to yet another embodiment of the present disclosure.
Figure 15B:
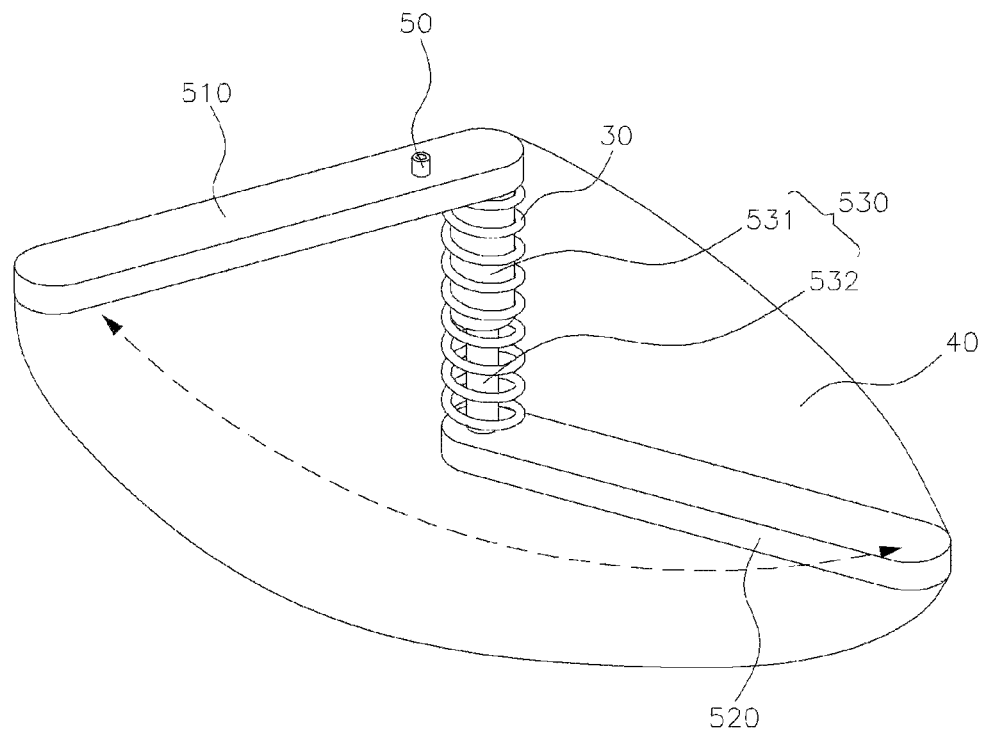
Figure 15C:
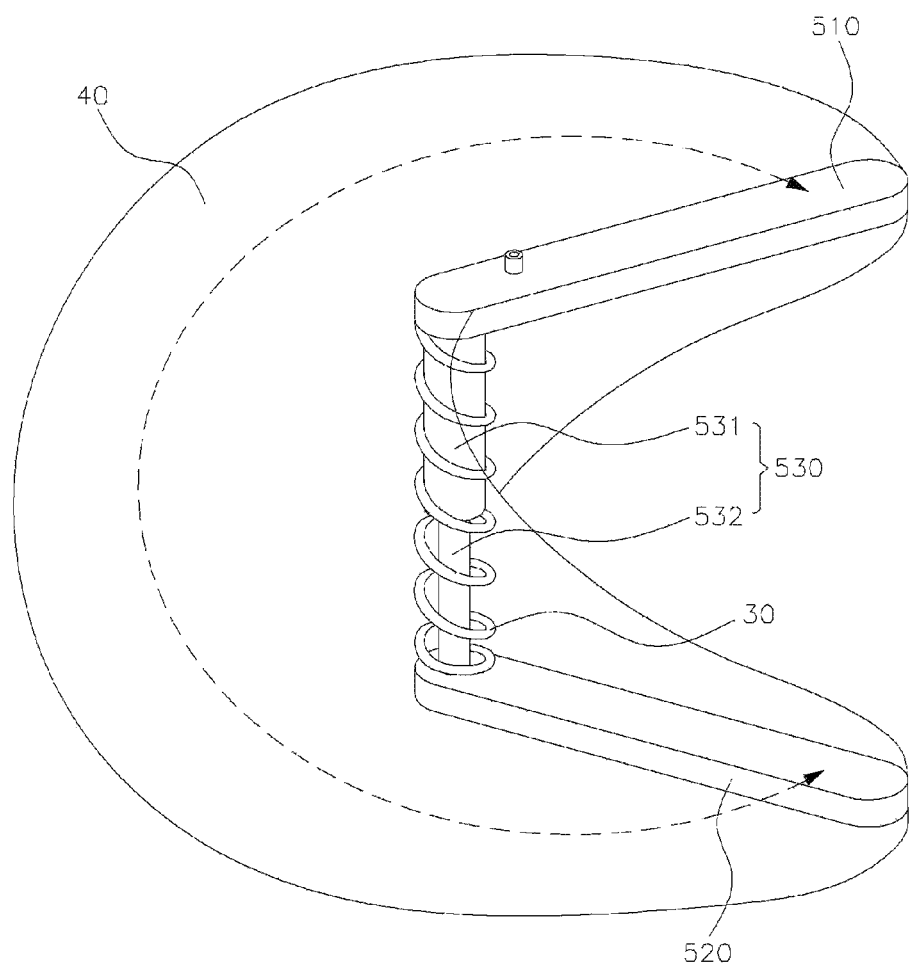

FIGS. 15A to 15C are views illustrating an operation process of a medical aspirator according to yet another embodiment of the present disclosure.

Referring to FIGS. 15A to 15C, the upper housing 510 and the lower housing 520 have a rod shape, the length of which is longer than the width thereof, and the screw thread connector 530 connects ends of the upper housing 510 and the lower housing 520.

The upper housing 510 is rotated with respect to the lower housing 520 as the coil spring 30 is expanded, and the sealing film 40 may be unfolded in a fan shape.

When the upper housing 510 and the lower housing 520 has a cylindrical shape, only rotation by up to 180 degrees may be performed, and the aspirator is vulnerable to a capacity or a change in a pressure.

Unlike this, when the sealing film 40 is unfolded in a fan shape, rotation by about 270 degrees or more may be performed, and the aspirator is excellent in terms of a capacity and a change in a pressure.

A process of operating the medical aspirator according to yet another embodiment of the present disclosure will be described below.

Referring to FIG. 15A, the upper housing 510 is pressed toward the lower housing 520. In this process, the inner screw thread connector 532 is inserted into the outer screw thread connector 531 and the coil spring 30 is compressed.

After the coil spring 30 is compressed, a separate fixing means configured to fix the upper housing 510 and the lower housing 520, such as a clip, may be provided.

Referring to FIG. 15B, as the fixing means is removed to operate the aspirator, the coil spring 30 is gradually expanded. Further, as the coil spring 30 is expanded, the upper housing 510 is rotated and lifted up by approximately 90 degrees with respect to the lower housing 520, and the sealing film 40 is unfolded in a fan shape.

Referring to FIG. 15C, the coil spring 30 is further expanded. Further, as the coil spring 30 is further expanded, the upper housing 510 is rotated and lifted up by approximately 260 degrees with respect to the lower housing 520.

In this process, the exudate 80 may be introduced through the suction port 50, and as the medical aspirator has a fan shape, a rotation angle increases, so that more excellent capacity efficiency may be achieved.

An optimum embodiment is disclosed in the above drawings and the above specification. Here, although specific terms are used, the terms are used to merely describe the present disclosure and are not used to delimit meaning or limit the scope of the present disclosure set forth in the appended claims. Therefore, it should be understood by those skilled in the art that various changes and equivalent other embodiments may be derived. Thus, the true technical protection scope of the present disclosure should be determined by the technical spirit of the appended claims.

The invention claimed is:

1. A medical aspirator having a constant suction pressure, the medical aspirator comprising:
   a hollow cylinder housing having a space formed in the cylinder housing;
   a piston slidable inside the cylinder housing in a longitudinal direction; and
   an elastic member having one end connected to the piston and the other end fixed to the cylinder housing, and allowing the piston to move in the longitudinal direction with a constant force,
   wherein the cylinder housing includes a guide rail connected to an outer surface of the cylinder housing and extending in the longitudinal direction, and a switch mounted on the guide rail.

2. The medical aspirator of claim 1, wherein the elastic member is a constant force spring.

3. The medical aspirator of claim 2, wherein the constant force spring includes a wound end and a fixed end.

4. The medical aspirator of claim 3, wherein a holder configured to fix the wound end is mounted on one end of the cylinder housing.

5. The medical aspirator of claim 1, wherein a stopper having a distal end protruding toward the space of the cylinder housing and having a rotational force such that the protruding distal end is rotatable toward an outside of the hollow is mounted on the hollow.

6. The medical aspirator of claim 5, wherein the switch is slidable in the longitudinal direction to determine whether the stopper is rotated.

7. A medical aspirator having a constant suction pressure, the medical aspirator comprising:
   an upper housing constituting an upper body;
   a lower housing constituting a lower body;
   a sealing film coupled along outer surfaces of the upper housing and the lower housing and having a space formed in the sealing film; and
   a screw thread connector connecting the upper housing and the lower housing and having a screw thread,
   wherein a coil spring is mounted on an outer circumferential surface of the screw thread connector,
   wherein the upper housing and the lower housing have a rod shape, a length of which is longer than a width, and
   wherein the upper housing is rotated and lifted up and the sealing film is unfolded in a fan shape by expanding of the coil spring.

8. The medical aspirator of claim 7, wherein the sealing film has a corrugated shape.

9. The medical aspirator of claim 7, wherein the screw thread connector includes,
   an outer screw thread connector coupled to the upper housing, and
   an inner screw thread connector coupled to the lower housing and is insertable into the outer screw thread connector.

10. The medical aspirator of claim 9, wherein screw threads having shapes complementary to each other are formed inside the outer screw thread connector and outside the inner screw thread connector, and
    wherein the screw threads are nonlinear screw threads.

11. The medical aspirator of claim 10, wherein a tangent slope of the screw threads increases as the screw threads near toward the upper housing.

12. The medical aspirator of claim 7, wherein the upper housing and the lower housing have a disc shape, and
    wherein the screw thread connector connects centers of the upper housing and the lower housing.

13. The medical aspirator of claim 7,
    wherein the screw thread connector connects ends of the upper housing and the lower housing.

* * * * *